United States Patent [19]

Goodbody et al.

[11] Patent Number: 4,918,011
[45] Date of Patent: Apr. 17, 1990

[54] ENZYMATIC PREPARATION OF 3',4'-ANHYDROVINBLASTINE

[75] Inventors: Anne E. Goodbody, Toronto; Endo Tsuyoshi, Mississauga; John Vukovic, Malton; Masanaru Misawa, Weston, all of Canada

[73] Assignee: Allelix Biopharmaceuticals Inc., Mississauga, Canada

[21] Appl. No.: 893,018

[22] Filed: Aug. 4, 1986

[51] Int. Cl.$^4$ .................. C12P 17/18; C12P 17/00; C12P 17/16
[52] U.S. Cl. .................... 435/119; 435/117; 435/118
[58] Field of Search ............... 435/117, 118, 119, 121, 435/190, 192; 540/478

[56] References Cited

U.S. PATENT DOCUMENTS

3,225,030  12/1965  Svoboda ........................ 260/236

OTHER PUBLICATIONS

Kutnet et al., "206, Biosynthesis of the Indole Alkaloids, Cell—free Systems from *Catharanthus roseus* Plants", Helvetica Chimica Acta, vol. 65, Fasc. 7, 2088–2101, 1982.
Kuthey, "Studies in Plant Tissue Culture: Potential Sources of Clinically Important Anti—Tumor Agents", Pure & Applied Chem., vol. 54, 2523–36, 1982.
Merck Index, p. 1231, #8423.
Heterocycles, vol. 9, No. 10, 1978—Stuart et al.
Pure & Applied Chem., vol. 54, No. 12, pp. 2523–2536, 1982, Kutney et al.
J. Org. Chem., vol. 44, No. 12, 1979, pp. 2052–2054, Trost et al.
Journal of the American Chemical Society 97:23, Nov. 1975, Ando et al.

*Primary Examiner*—Charles F. Warren
*Assistant Examiner*—Gail E. Poulos
*Attorney, Agent, or Firm*—Wyatt, Gerber, Burke and Badie

[57] ABSTRACT

3',4'-anhydrovinblastine, a precursor of the anti-tumor alkaloids vincristine and vinblastine, is prepared by the enzymatic coupling of catharanthine and vindoline using an iron-containing compound such as peroxidase optionally in the presence of a peroxide. Substantially enhanced yields are obtained.

15 Claims, 2 Drawing Sheets

ENZYMATIC PREPARATION OF 3',4'-ANHYDROVINBLASTINE

FIELD OF THE INVENTION

This invention relates to alkaloid compounds useful as anti-tumour agents and as precursors of anti-tumor agents, and processes for their preparation. More specifically, it relates to the preparation of 3',4'-anhydrovinblastine, a precursor of the known and approved anti-tumor alkaloids vincristine and vinblastine, by enzymatic reaction.

BACKGROUND OF THE INVENTION

A number of naturally occurring alkaloids found in the Madagascar periwinkel plant *Catharanthus roseus* (also known as *Vinca rosea* and *Lochnera rosea*) are approved anti-tumor drugs. Of prime commercial interest are vincristine and vinblastine which are accepted in the treatment of cancers. Vincristine is an active agent in the treatment of leukemia, lymphomas and solid tumours. Vinblastine has similar activity, and is also an active agent in the treatment of Hodgkin's disease.

Both vinblastine and vincristine are currently obtained by extraction from the plants, which have to be harvested and dried before the drugs can be extracted. The complexity of the plant extract (containing at least 200 different alkaloids) and the low concentrations of the desired alkaloids (0.0003% dry weight for vinblastine) make the extraction process both lengthy and expensive. The problems inherent in the extraction procedure make the development of alternative methods of vincristine and vinblastine production attractive.

Vincristine can be prepared chemically from vinblastine. In turn, vinblastine can be prepared chemically from catharanthine and vindoline, both natural indole alkaloids found in the *Catharanthus roseus* plant, via an intermediate material, 3',4'-anhydrovinblastine (A-VLB). Catharanthine and vindoline can be chemically coupled together using a peracid (e.g. m-chloroperbenzoic acid) to convert catharanthine to its N-oxide, followed by a Polonovski-type fragmentation of the N-oxide initiated with addition of trifluoroacetic acid to form a natural dimer. A reducing agent such as sodium borohydride is then added to the mixture to produce 3',4'-anhydrovinblastine (A-VLB) which can be converted to vinblastine, and thence to vincristine, by further oxidation. The overall chemical reaction scheme can be represented thus:

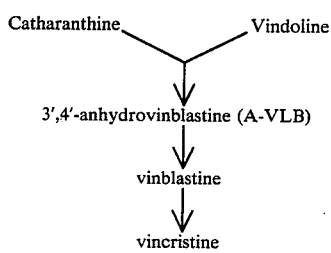

3',4'-anhydrovinblastine (A-VLB), has itself been reported to have a potent cytostatic activity, and indeed shows lower toxicity than either vincristine or vinblastine. It is an essential precursor of vinblastine and vincristine synthesis. Kutney "Pure and Applied Chemistry", 54, 2523 (1982) and "Heterocycles" 9, 1419 (1978) has shown that A-VLB can be formed enzymatically from vindoline and catharanthine using cell-free extracts from *C. roseus* leaves. The yields reported are, however, extremely low.

The chemical coupling reaction of chatharanthine and vindoline, in simplified form, can be represented as follows:

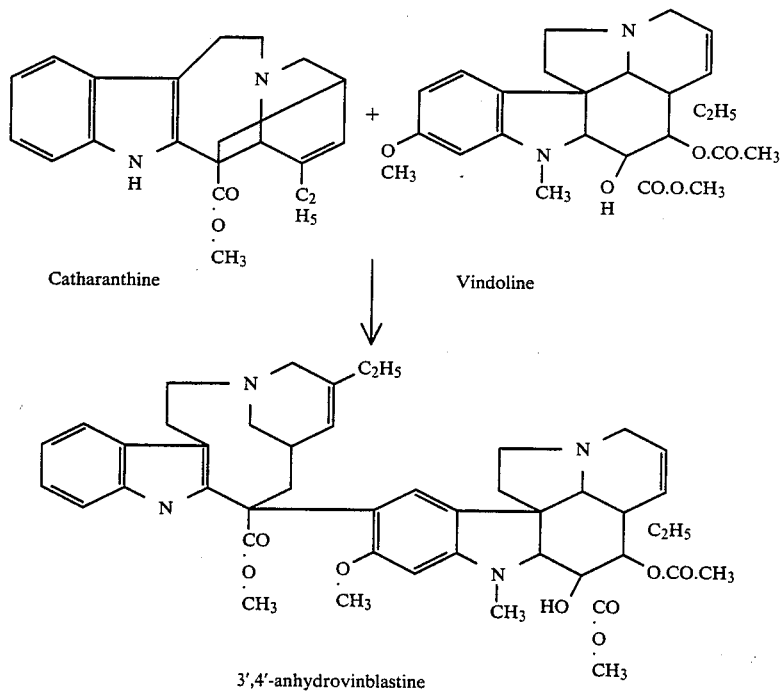

It is an object of the present invention to provide a novel enzymatic process for the preparation of 3',4'-anhydrovinblastine from catharanthine and vindoline.

SUMMARY OF THE INVENTION

In the present invention, A-VLB is prepared in substantially improved yields, by a process which involves the step of coupling together catharanthine and vindoline in the presence of a catalytically effective amount of an iron-containing compound the iron component of which is able to participate in an oxidation-reduction type of reaction. Such compounds include the heme-containing compounds such as the enzymes peroxidase and microperoxidase as well as non-proteinaceous compounds such as hemin. In addition, the reaction mixture desirably contains peroxide, the source of which may vary from stock hydrogen peroxide to enzyme cofactors such as flavin mononucleotide (FMN) together with $MnCl_2$ which are believed to generate peroxide in vitro. A $Mn^{2+}$ source may be added to the peroxidase and peroxide but is not essential.

As used herein, the term "heme" is used to mean both $Fe^{2+}$ and $Fe^{3+}$-containing prosthetic groups e.g. the protoporphyrin IX group.

The present invention is predicated on the identification of components within *C. roseus* cell-free extracts which act to couple the reactants to form A-VLB in vivo. It has been discovered that, of the *C. roseus* cellular components, it is the peroxidase, in any of its isozymic forms, together with a peroxide presumably generated by FMN and $Mn^{2+}$ (as $MnCl_2$) through a light mediated reaction which couples vindoline and catharanthine to produce A-VLB.

The in vitro reaction is believed to progress firstly by forming a hydroperoxyindolenine derivative of catharanthine in the presence of peroxidase. Then the hydroperoxyindolenine and vindoline couple to form an iminium intermediate. Subsequent reduction produces A-VLB, in all likelihood.

On that basis and from these and subsequent observations, the scope of the present invention encompasses the use of enzymes additional to *C. roseus*-derived peroxidases and peroxide sources additional to FMN and $Mn^{2+}$ although these compounds are useful. The present invention comprises such readily and commercially available compounds as horseradish peroxidase, microperoxidase and hemin which may be used in place of the *C. roseus*-derived peroxidases. Further, the peroxide source may simply be stock hydrogen peroxide.

From present observations, it is evident that peroxide is not always necessary in the reaction medium. A-VLB is formed in minor but still significant amounts without peroxide addition such as when microperoxidase and hemin are used. Yields are enhanced when peroxide is present, however and its addition or in vitro generation is therefore desirable.

Because of the oxidative nature of the reaction medium in which coupling occurs, it is most desirable to halt the reaction by addition of a reducing agent at a time when coupling is at a maximum. Further oxidation can result in other undesired alkaloids such as leurosine. Reaction timing is therefore important but can be controlled by manipulation of enzyme and substrate concentration as well as by temperature control etc. Further, reaction progress can be monitored if desired.

By identifying those components which operate in vivo to produce A-VLB, the reaction can be optimized, allowing for enhanced yields e.g. up to 40% of theoretical as compared with lower yields using cell-free extracts of *C. roseus*. Moreover, the reaction is "cleaner" in many ways. For example, the product is more easily isolated in pure form than when entire cell-free extracts are used. This is significant given the pharmaceutical nature of A-VLB and the products such as vinblastine which are produced from A-VLB. There is less risk of contamination by toxic impurities. Further, reaction inhibitors which may be present in the cell-free extract are removed. By increasing yield of A-VLB, subsequent yield of derivatized A-VLB products like vinblastine are also enhanced in the overall process scheme.

DETAILED DESCRIPTION OF THE PREFERRED EMBODIMENTS

Figure 1:
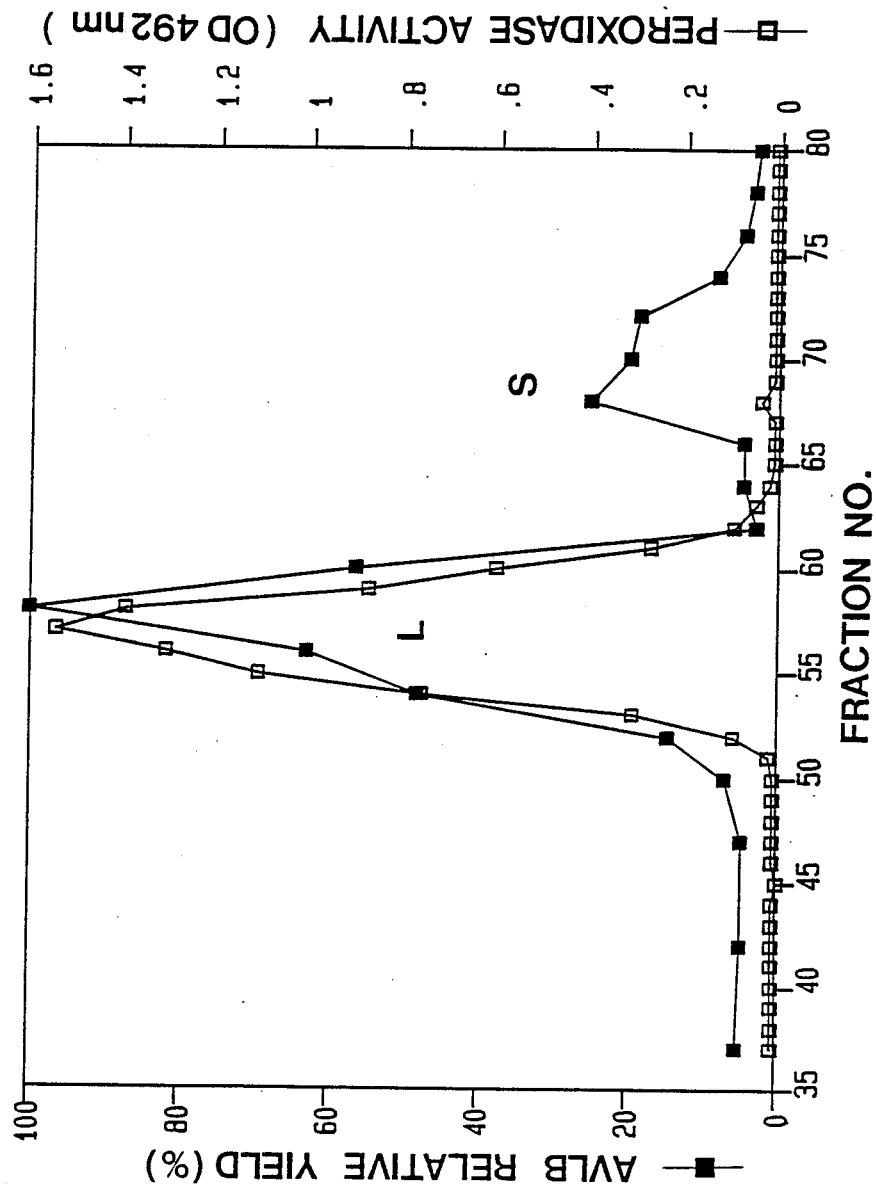

All of the reactants and reagents required in the process are available either commercially or through standard laboratory techniques.

The reactants vindoline and catharanthine can be purchased although they can be extracted from *C. roseus* tissue independently, if desired, using techniques standard in the art. (see, for example, Andol et al. *J. Am. Chem. Soc.* 97,6880 (1975) and B. M. Trost et al, *J. Org. Chem.*, 44,2052 (1979) respectively.)

Microperoxidase, hemin and horseradish peroxidase, preferred for use herein for economic reasons, are also commercially available. The peroxidases derived from *C. roseus* can be extracted using standard techniques further exemplified herein. In general, phenolics are removed from cell extracts of *C. roseus* cells which are derived either from callus tissue or a cell suspension, preferably from cell suspension, and the resultant composition centrifuged to obtain a protein-containing supernatant. Proteins are then precipitated such as by ammonium sulfate treatment and then desalted to form a crude enzyme extract. Thereafter, various filtrations and separations are conducted in order to obtain those proteins which have the characteristic isoelectric points and activities described in detail in the examples. Five isozymes of *C. roseus* have been identified, any of which may be used for the purposes of this invention.

Hydrogen peroxide may be purchased as may flavin mononucleotide (FMN) and any suitable salt of $Mn^{2+}$ such as $MnCl_2$. For use herein, hydrogen peroxide is the preferred peroxide source.

To conduct the reaction, vindoline and catharanthine are admixed in buffer, preferably Tris-HCl, to maintain a pH ranging from about 5 to 7 and more preferably, a mildly acidic pH from 6 to 7. The reaction medium is incubated at about 30° C. to accomodate the enzyme although, as mentioned, temperature control may be utilized to manipulate enzyme efficiency and reaction progress so that temperatures may range widely. The reaction is initiated either by peroxide or by peroxidase addition and the reaction allowed to proceed until maximum conversion to A-VLB is attained, usually in about 45–75 minutes under the experimental conditions described herein. This reaction rate can be controlled, however, as desired. Once A-VLB has been generated in desired amounts, a reducing agent such as sodium borohydride may be added to halt subsequent oxidation of A-VLB to leurosine. To determine when maximum coupling has occurred, it is necessary simply to perform a time course study on reaction progress.

There are preferred ratios of enzyme to substrate (vindoline, catharanthine and $H_2O_2$) which are calibrated to strike a balance between fast A-VLB production and the need to isolate A-VLB within the precise time period when its accumulation is at a maximum. While the peroxidase:catharanthine:vindoline:$H_2O_2$ ratios i.e. enzyme:substrate, ratio can range from $10^{-9}$:1 to 1:1 more practical ratios preferred herein are $3\pm1.5\times10^{-3}$:1 when either microperoxidase, horseradish peroxidase or any of the five *C. roseus* peroxidase isozymes are used. However, optimum coupling was found with a ten-fold increase in hemin concentration, when hemin was used.

When it is desired to add the manganese ion to reaction medium, it is suitably added prior to enzyme introduction, to achieve concentrations ranging from 50 to 2,000 μM, more preferably 500-1,500 μM and ideally at 1,000 μM.

Where the combination of $FMN/Mn^{2+}$ is used in place of $H_2O_2$ as a peroxide source, the FMN is added to achieve a medium concentration of 50-2,000 μM more preferably 500-1,500 μM. It is important to bear in mind that when FMN is involved in the reaction, it is most desirable to conduct the process in the light.

The recovery and assay of the dimeric alkaloids from the coupling reaction medium may be accomplished by techniques of thin layer chromatography. Prior to analysis and recovery of the dimeric alkaloid products, the extracts may be purified e.g. using column gel permeation chromatography to remove excess unreacted starting materials vindoline and catharanthine and to remove other alkaloids, thereby separating the compounds on the basis of molecular weight. HPLC systems of separation may also be used to separate and purify the products. The extraction of the reaction medium is suitably done by adjusting the pH of the mixture to about 9 with concentrated ammonium hydroxide, and then extracting the mixture three times with ethyl acetate. The pooled ethyl acetate fractions may then be dried down and the residue dissolved in methanol for analysis.

In the TLC analysis and separation process, appropriate solvent systems for use therein include toluene: acetone: methanol: ammonium hydroxide, and diethylether: chloroform: methanol. After the samples have been chromatographed by TLC they may then be examined with a TLC scanner, mixtures separated by HPLC may be analysed by means of UV absorbtion for product identification and quantity measurements. Analysis of the products may also be conducted by mass spectrometry techniques.

Figure 2:
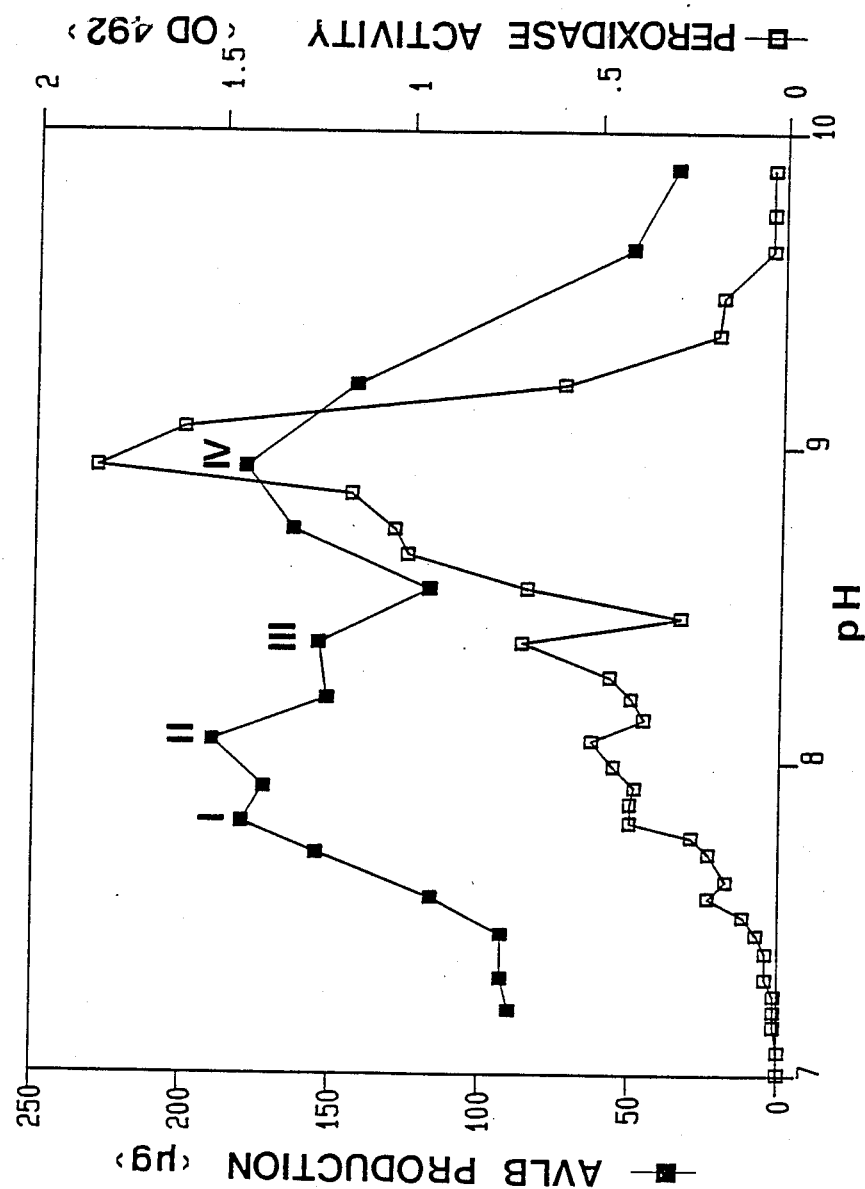

Embodiments of the invention are described hereinafter by way of example only with reference to;

FIGS. 1 and 2 which are referred to in Example 1.

EXAMPLE 1

Recovery of *C. roseus* Peroxidases

A cell line of *C. roseus* designated JWM* was used as the enzyme source. This line was developed for plant tissue culture specifically. Other similar lines are available. Two week old suspension cultures were harvested and stored at $-20°$ C.

The frozen cells were ground in a chilled mortar with equivalent weight of PVPP and two volumes of Tris-HCl buffer (pH 6.8, 100 mM). The extract was centrifuged at $10,000\times g$ for 20 minutes and then protein was precipitated from the supernatant with 70% saturated $(NH_4)_2SO_4$. The protein pellet was dissolved in Tris-HCl buffer and desalted with BioGel P6 equilibrated with the same buffer. This protein solution was frozen and stored at $-20°$ C. until used.

The desired solution (30 ml) was restored and put on the top of a DEAE Fractogel column ($2.5\times2$ cm, bed volume 10 ml) and eluted with the same buffer. Active enzyme was eluted in the first 45 ml fraction while more than 65% of the protein was adsorbed on the ion exchange gel.

The active fraction was applied to a Sephacryl S-200 column ($2.2\times200$ cm, bed volume 980 ml) equilibrated with the Tris-HCl buffer. The protein was eluted, at a flow rate of 20 ml/hr., and fractions of 10 ml were collected. The activity appeared as two peaks (L and S) as can be seen in FIG. 1. Each of these fractions (70 ml) was concentrated with ultrafiltration (Amicon, 5,000 MW cutoff) to 20 ml and desalted with a Biogel P-6 column equilibrated with water.

Concentrated fraction L and S were separately applied to a density gradient isoelectric focusing column (LKD, 110 ml) containing 1% carrier ampholyte (pH3-10:pH6-8 = 1:4, Pharmacia), and run at 800 V for 36 hours.

The coupling activity of the enzyme was also tested in the following manner. The reaction mixture contained enzyme, 0.5 mg catharanthine HCl, 0.5 mg vindoline, 1 mM FMN (or 0.15 mM Hydrogen peroxide), and 1 mM $MnCl_2$ in 6 ml Tris-HCl buffer (100 mM, pH 6.8). The incubation was done at $30°$ C. for 1 hr. The reaction was stopped by adding 28% $NH_4OH$ (to pH 9.5). Before the alkaloids were extracted with ethyl acetate by phase partitioning, excess amount of $NaBH_4$ was added to the reaction mixture to recover AVLB. AVLB was quantified with TLC (solvent system, Diethylether:Chloroform:Methanol = 50:35:20) scanned at 280 nm.

The results appear in Table 1 below.

TABLE 1

| Purification procedure | | | |
|---|---|---|---|
| | Total Protein (mg) | Specific Activity (μmol AVLB/he/mg) | Purification |
| crude | 2550 | | |
| 70% $(NH_4)_2$ SO | 2340 | 0.260 | 1.00 |
| DEAE fractogel | 810 | 0.260 | 2.65 |
| [Fraction L] | | | |
| S 200 | 191 | 0.512 | 5.22 |
| isoelectric focusing | | | |
| L-I | 0.679 | 21.0 | 214 |
| L-II | 0.758 | 15.1 | 154 |
| L-III | 0.833 | 16.9 | 172 |
| L-IV | 1.04 | 18.8 | 192 |
| [Fraction S] | | | |
| S 200 | 19.5 | 1.23 | 12.5 |
| isoelectric focusing | 0.36 | 13.1 | 134 |

Estimation of molecular weight

The molecular weight of purfied enzymes were estimated by HPLC (Waters 840) gel filtration system. The conditions for gel filtrations were; columns of Protein Pak 125 and Protein Pak 60 in series, Tris-HCl (100 mM, pH 7.0) eluting buffer, and a flow rate of 1 ml/min. Protein was monitored at 280 nm and 405 nm. The results appear in Table 2 below.

TABLE 2

| Purified Coupling Enzymes from *C. roseus* Cells | | |
|---|---|---|
| Enzyme | Molecular Weight | pI |
| L-I | 37,000 | 7.8 |
| L-II | 37,000 | 8.0 |
| L-III | 37,000 | 8.3 |
| L-IV | 37,000 | 9.0 |
| S | 15,000 | 10.5 |

After each separation, the peroxidase activity of the fractions was determined by incubation of fractions with orthophenylenediamine (0.4 mg/ml) and 3% hydrogen peroxide (10 μl/ml) in Tris-HCl buffer (100 mM, pH 6.8) at room temperatuare for 10 minutes in the dark. The reaction was stopped by adding 5N HCl (0.1 ml/ml), then absorbance at 492 nm was measured. The results after each separation step appear in Table 3 below.

TABLE 3

| | Specific Activities | | |
|---|---|---|---|
| Enzyme | (A) Coupling $H_2O_2$ (μnol/hr/mg) | (B) Peroxidase OPD (OD492/10 min/mg) | (A)/(B) |
| L-I | 8.41 | 0.88 | 9.5 |
| L-II | 13.5 | 1.01 | 13.4 |
| L-III | 14.7 | 1.24 | 11.9 |
| L-IV | 28.3 | 2.66 | 10.6 |

The results of the coupling activity as well as peroxidase activity are shown graphically in FIGS. 1 and 2. It will be noted that coupling activity and peroxidase activity were closely associated. This indicates the peroxidase nature of the purified enzymes catalyzing coupling.

EXAMPLE 2

Anhydrovinblastine Production from Catharanthine and Vindoline and Hydrogen Peroxide Using Horseradish Peroxidase

| | Final Conc. (μM) | | |
|---|---|---|---|
| Horseradish Peroxidase (Type I; Sigma) | 0.17 | 0.5 | 0.8 |
| Catharanthine Sulphate | 300 | 300 | 300 |
| Vindoline | 300 | 300 | 300 |
| Hydrogen Peroxide | 300 | 300 | 300 |

This was made up in Tris buffer (0.1M, pH 7.0) to a final volume of 2.5 ml. The incubation was performed at 30° C. and the reaction was initiated by addition of the hydrogen peroxide. After 45 minutes it was stopped with sodium borohydride (50 μl of a 2 mg/ml aqueous solution). This was then made alkaline through addition of 50 μl of concentrated ammonium hydroxide and then extracted 3 times with ethyl acetate. The ethyl acetate was dried down and taken up in 200 μl methanol for analysis.

Analysis

HPLC: Samples were eluted on an RP-8 reverse phase column using a gradient of methanol and water. Two peaks were identified as being 3',4'-anhydrovinblastine, i.e. retention times and UV spectra were identical to those of authentic standards.

TLC: Samples were run on silica gel plates with a solvent system of diethylether:chloroform:methanol (50:35:20). Two spots were identified as being 3',4'-anhydrovinblastine and leurosine i.e. Rf values and UV spectra were identical to those of authentic standards. When the plate was sprayed with ceric ammonium sulphate spray, the characteristic colours of anhydrovinblastine and leurosine were observed.

Mass Spectrophotometry: The presence of 3',4'-anhydrovinblastine was confirmed with high resolution mass spec data.

| | Results from HPLC data | | |
|---|---|---|---|
| | Yield (% of Substrates Added) | | |
| μM Enzyme | A-VLB | Leur | Total |
| 0.17 | 2.5 | 0 | 2.5 |
| 0.5 | 13.8 | 2.7 | 16.5 |
| 0.8 | 25.6 | 4.8 | 30.4 |

EXAMPLE 3

Other Heme Substances

Incubations were made up as for Example 2 and all other conditions and procedures were the same. Three different concentrations of hemin were tested: 0.5, 5 and 50 μM. Best results occured with 5 μM.

| | Conc (μM) | Yield (% of Substrates) | | |
|---|---|---|---|---|
| | | A-VLB | Leurosine | Total |
| Hemin | .5 | 3.0 | 2.3 | 5.3 |
| | 5 | 28.3 | 4.1 | 32.4 |
| | 50 | 17.4 | 2.8 | 20.2 |
| Microperoxidase | 0.5 | 29.1 | 3.2 | 32.3 |
| Hemoglobin | 0.125 (conc. of heme = 0.5 μM) | 1.5 | 0.8 | 2.7 |

(Results from HPLC)

From these results it is evident that the coupling reaction can be performed in the presence of several sources of heme, even in the absence of protein. Microperoxidase (MP-11) is a part of cytochrome c: 10 amino acids with a heme group attached. A ten-fold increase in haemin concentration is required in order to obtain yields similar to that of microperoxidase and horseradish peroxidase, under these conditions.

EXAMPLE 4

Anhydrovinblastine Production from Catharanthine and Vindoline Using Horseradish Peroxidase (with FMN and $MnCl_2$)

| | Final Conc, (μM) |
|---|---|
| Horseradish Peroxidase | 0.42 |
| Catharanthine HCl | 224 |
| Vindoline | 183 |
| FMN | 697 |
| $MnCl_2$ | 1000 |

The incubation was made up as shown above in 0.1M Tris (pH 7.0) to a final volume of 6 ml. It was incubated at 30° C. for 1.25 hr. The reaction mixture was stopped and extracted as described previously. In the results below, a comparison is shown with $H_2O_2$ (0.15 mM) in place of FMN and $MnCl_2$.

| | Yield (% of Substrates) | | |
|---|---|---|---|
| | A-VLB | Leurosine | Total |
| FMN + $Mn^{2+}$ | 10.7 | 2.1 | 12.8 |
| $H_2O_2$ | 18.0 | 4.2 | 22.2 |
| | | | (HPLC data) |

These results show that the presence of FMN and $Mn^{2+}$ also enable coupling to occur. This is a light-sensitive reaction. The results below show the effect of light on the reaction. The proportions of the mixture were slightly different from those shown above.

|  | Final Conc. ($\mu$M) |
|---|---|
| Horseradish Peroxidase | 0.5 |
| Catharanthine SO$_4$ | 150 |
| Vindoline | 150 |
| FMN | 837 (1 mg) |
| MnCl$_2$ | 1000 |

The reaction mixture was made up to a final volume of 2.5 ml in 0.1M Tris buffer (pH 7.0) and incubated for 1.25 hr. The reaction was stopped and extracted as before.

| | Yield (% of Substrates) | | |
|---|---|---|---|
| | A-VLB | Leurosine | Total |
| Light | 11.9 | 0.9 | 12.8 |
| Dark | 3.2 | 0.6 | 3.8 |
| | | | (HPLC data) |

EXAMPLE 5

The coupling activity of enzyme L-I in the presence of FMN+MnCl$_2$ is compared with activity in the presence of H$_2$O$_2$ in Table 4 below.

TABLE 4

| | AVLB Yield ($\mu$g) |
|---|---|
| FMN + MnCl$_2$ | 279 |
| Hydrogen peroxide + MnCl$_2$ | 362 |
| Hydrogen peroxide | 340 |
| Enzyme; L-Ig (50 $\mu$g/5 ml) | |
| Incubation; 75 min at 30° C. | |
| FMN conc. = 1.0 mM | |
| Hydrogen peroxide conc. = 0.15 mM | |
| Manganous chloride conc. = 1.0 mM | |
| Catharanthine HCl = 0.5 mg/5 ml | |
| Vindoline = 0.5 mg/5 ml | |

Thus, different peroxide sources are able to function in coupling catharanthine and vindoline.

EXAMPLE 6

The maximum yields of A-VLB obtained with the various enzymes is given below as are the reaction conditions.

| Maximum Yields of A-VLB Obtained with Different Enzymes | | |
|---|---|---|
| Enzyme | A-VLB Yield ($\mu$g) | % |
| L-I | 438 | 43.8 |
| L-II | 436 | 43.6 |
| L-III | 447 | 44.7 |
| L-IV | 495 | 49.5 |
| S | 431 | 43.1 |
| HRP | 365 | 36.5 |

Incubation; 75 min at 30° C.
Reaction mixture contained 0.15 mM hydrogen peroxide, 1.0 mM manganous chloride, 0.5 mg catharanthine HCl, 0.5 mg vindoline, and 0.1 mg enzyme.
HRP; Horseradish peroxidase (Sigma).

EXAMPLE 7

To determine whether peroxide or a peroxide source is required in the reaction medium, enzyme was reacted with 300 $\mu$M catharanthine sulphate and 300 $\mu$M vindoline either with or without 300 $\mu$M H$_2$O$_2$. The results are shown below.

| Enzyme | H O | A-VLB | Leurosine | Total |
|---|---|---|---|---|
| 5 $\mu$M Hemin | + | 10.4 | 1.6 | 12.0 |
| | − | 5.4 | 1.1 | 6.5 |
| 10 $\mu$M Microperoxidase | + | 30.7 | 1.8 | 32.5 |
| | − | 14.2 | 1.4 | 15.6 |

It is evident therefore that while H$_2$O$_2$ is not an essential reaction component, its presence substantially enhances yield when microperoxidase and hemin are used.

What is claimed is:

1. A process for preparing 3',4'-anhydrovinblastine which comprises forming a reaction mixture containing vindoline, catharanthine and a catalytically effective amount of a coupling agent selected from the group consisting of hemoglobin, hemin, microperoxidase and horseradish peroxidase.

2. The process according to claim 1 wherein the reaction mixture further comprises a 3',4'-anhydrovinblastine yield-enhancing amount of peroxide.

3. The process according to claim 1 wherein the coupling agent is horseradish peroxidase.

4. The process according to claim 2 wherein peroxide is either hydrogen peroxide or is generated in situ by a flavin mononucleotide and manganous ion light mediated reaction.

5. The process according to claim 4 wherein peroxide is hydrogen peroxide.

6. The process according to claim 1 wherein the horseradish peroxidase is present in a molar ratio of from $10^{-9}$ to 1 moles per mole of substrate.

7. The process according to claim 3 wherein the horseradish peroxidase is present in a molar ratio of from $1.5 \times 10^{-3}$ to $4.5 \times 10^{-3}$ moles per mole of substrate.

8. The process according to claim 1 including the step of adding, at a terminal stage of the process, a reducing agent to the reaction mixture.

9. The process according to claim 8 wherein the reducing agent is sodium borohydride.

10. The process according to claim 1 including the step of recovering 3',4'-anhydrovinblastine from the reaction mixture.

11. A method for obtaining 3',4'-anhydrovinblastine in enhanced yields which comprises forming a reaction mixture containing vindoline, catharanthine, and an effective amount of horseradish peroxidase as a coupling agent, adding a reducing agent thereto when it is desired to halt reaction progress and recovering 3',4'-anhydrovinblastine therefrom.

12. The method according to claim 11 wherein the reaction mixture further comprises a 3',4'-anhydrovinblastine yield-enhancing amount of peroxide.

13. The method according to claim 12 wherein the peroxide is hydrogen peroxide.

14. The method according to claim 11 wherein the reducing agent is sodium borohydride.

15. A process for obtaining 3',4'anhydrovinblastine which comprises forming a reaction mixture containing vindoline, catharanthine, horseradish peroxidase and hydrogen peroxide, adding sodium borohydride to the reaction mixture when the 3',4-anhydrovinblastine yield is substantially at a maximum and then recovering 3',4'-anhydrovinblastine from the reaction mixture.

* * * * *